US005731443A

United States Patent [19]

Dengler et al.

[11] Patent Number: 5,731,443
[45] Date of Patent: *Mar. 24, 1998

[54] LIQUID PHTHALIC ANHYDRIDE RECOVERY PROCESS USING A RECTIFICATION TOWER

[75] Inventors: Herbert Peter Dengler, Baton Rouge, La.; James Joseph Baiel, Morris Plains, N.J.

[73] Assignee: Exxon Chemical Patents Inc., Houston, Tex.

[*] Notice: The term of this patent shall not extend beyond the expiration date of Pat. No. 5,508,443.

[21] Appl. No.: 431,647

[22] Filed: May 2, 1995

Related U.S. Application Data

[63] Continuation-in-part of Ser. No. 241,876, May 12, 1994, Pat. No. 5,508,443.

[51] Int. Cl.⁶ .................................................. C07D 307/89
[52] U.S. Cl. .................. 549/248; 549/250; 549/239; 549/245; 549/256; 549/262; 560/494
[58] Field of Search ........................ 549/248, 250

[56] References Cited

U.S. PATENT DOCUMENTS

| | | | |
|---|---|---|---|
| 2,098,047 | 11/1937 | Jaeger et al. | 260/122 |
| 3,178,452 | 4/1965 | Smith et al. | 260/346.4 |
| 3,303,203 | 2/1967 | Melnstein | 260/346.7 |
| 3,380,896 | 4/1968 | Scheiber et al. | 203/77 |
| 3,397,121 | 8/1968 | Fitzgerald | 203/35 |
| 3,507,886 | 4/1970 | Suter et al. | 260/346.7 |
| 3,650,906 | 3/1972 | Gehrken et al. | 203/89 |
| 3,655,521 | 4/1972 | Gehrken et al. | 203/28 |
| 3,681,399 | 8/1972 | Barth | 260/346.7 |
| 3,725,211 | 4/1973 | Gehrken et al. | 203/74 |
| 4,285,870 | 8/1981 | Keuncke et al. | 260/346.7 |
| 4,285,871 | 8/1981 | Keunecke et al. | 260/346.7 |
| 4,568,427 | 2/1986 | Danz et al. | 203/42 |
| 5,214,157 | 5/1993 | Healy et al. | 549/250 |
| 5,508,443 | 4/1996 | Dengler et al. | 549/258 |

FOREIGN PATENT DOCUMENTS

| | | | |
|---|---|---|---|
| 1121645 | 4/1956 | France | 14/1 |

*Primary Examiner*—Bernard Dentz
*Attorney, Agent, or Firm*—John F. Hunt

[57] ABSTRACT

A process for recovering phthalic anhydride as a liquid from a vapor phase oxidation product which comprises mixing the vapor phase oxidation product having a temperature in the range of about 130° C. or greater with a first stream comprising maleic anhydride and/or at least one compound selected from the group consisting of: citraconic anhydride, benzoic acid and phthalic anhydride in a rectification tower such that a substantial portion of the phthalic anhydride contained within the vapor phase oxidation product transfers from the vapor phase to a liquid phase and the by-products contained in the first stream which are more volatile than phthalic anhydride transfer from the liquid phase to the vapor phase and wherein a vapor-to-liquid weight ratio in the range between about 5 to 20 is exhibited within the rectification tower, thereby forming a liquid phase phthalic anhydride product having a phthalic anhydride concentration in the range between about 50–100 wt. %, preferably 90–100 wt. %, without the formation of an intermediate solid phase.

17 Claims, 4 Drawing Sheets

LIQUID PHTHALIC ANHYDRIDE RECOVERY PROCESS USING A RECTIFICATION TOWER

This is a continuation-in-part of application Ser. No. 08/241,876, filed May 12, 1994 now U.S. Pat. No. 5,508,443.

The present invention generally relates to a method and system for continuously recovering liquid phase phthalic anhydride from a vapor phase oxidation product without the formation of a solid phase. In particular, phthalic anhydride is recovered from the vapor phase oxidation product by contacting this gaseous oxidation product with recycled maleic anhydride and/or other by-products in a rectification tower so that the condensate does not solidify and so that a vapor-to-liquid weight ratio in the range between about 5 to 20 is maintained, thereby eliminating the need for switch condensers. In this way the more volatile by-products are taken overhead from the separation vessel as a vapor, while phthalic anhydride is taken out as bottoms without the formation of a solid phase during the separation.

BACKGROUND OF THE INVENTION

Phthalic anhydride is an important commercial chemical useful in the manufacture of plasticizers, polyesters, alkyd resins and dyes.

Phthalic anhydride is typically produced from raw materials such as orthoxylene (o-xylene), petroleum naphthalene, and coal-tar naphthalene. Various well known processes are currently being used in the production of phthalic anhydride, i.e., (1) air oxidation of o-xylene in fixed-bed reactors, (2) air oxidation of petroleum or coal tar naphthalene in fixed-bed reactors, (3) fluid bed oxidation of o-xylene, (4) fluid bed oxidation of petroleum or coal tar naphthalene, and (5) liquid phase oxidation of o-xylene or naphthalene.

U.S. Pat. No. 5,214,157 (Healy et al.), which issued on May 25, 1993, is incorporated herein by reference and generally discloses the formation of phthalic anhydride via the vapor phase oxidation of o-xylene. In accordance with the process described in U.S. Pat. No. 5,214,157, o-xylene and air are catalytically converted into a vapor phase oxidation product, i.e., a reaction gas composed of nitrogen, oxygen, water, carbon dioxide, carbon monoxide, phthalic anhydride, maleic anhydride, maleic acid, benzoic acid, o-toluic acid, and partial oxidation products such as phthalide. This vapor phase oxidation product is typically first cooled to generate steam and then delivered to expensive switch condensers, where it is cooled to permit the desublimation of a crude phthalic anhydride stream from the gas. Thereafter, the crude phthalic anhydride is sent to a finishing section in order to produce substantially pure phthalic anhydride.

The switch condensers operate alternatively on cooling and heating cycles in order to first collect the phthalic anhydride as a solid and then melt it for removal from the condensers. The use of switch condensers to separate crude phthalic anhydride from a vapor phase oxidation product is also described in U.S. Pat. No. 5,214,157, which is incorporated herein by reference. Typically, the reactor vapor phase oxidation product is cooled close to the solidification point 131° C. (268° F.) of phthalic anhydride and any condensed liquid is separated out before the remaining vapor enters the switch condensers. The switch condensers desublime the vapor phase oxidation product using the cold condenser oil, and then melt off the solid phase crude phthalic anhydride product using a hot condenser oil heated with steam.

A substantial mount of impurities exit switch condensers as part of the vapor stream, whereas the crude phthalic anhydride product is plated out on the heat exchange tubes as a solid during the cooling step and exits the switch condensers at the bottom as a liquid during the melting step. The vapor gases from the switch condensers are sent to waste gas incinerators where the by-products are destroyed by oxidation to carbon dioxide and water.

Unfortunately, switch condensers contribute to a significant portion of the capital and operating costs of a phthalic anhydride plant. Also, switch condensers operate in a batch mode on 3–6 hours cycles to desublime solid phthalic anhydride on the heat exchange tubes. Another problem associated with switch condensers is that they necessitate frequent maintenance which requires that designated switch condensers be taken out of service on a periodic basis. Maintenance of switch condensers is costly due to the high labor requirement and condenser down time.

The present inventors have developed a unique process scheme which avoids the need to use expensive switch condensers to recover the phthalic anhydride from the vapor phase oxidation product. This unique process continuously condenses and recovers phthalic anhydride by rectification without the formation of an intermediate solid phase, wherein the more volatile by-products are taken overhead.

The continuous liquid recovery process of the present invention provides the following advantages over conventional switch condensers: (1) fewer pieces of processing equipment; (2) continuous rather than a batch mode of operation; (3) higher recovery of the phthalic anhydride from the vapor phase oxidation product; (4) an economic advantage which increases with higher concentrations of organics in the vapor phase oxidation product; (5) provides concentrated liquid maleic anhydride, citraconic anhydride and benzoic acid by-product streams which could be upgraded for commercial sale; and (6) benefits the environment since the waste gas contains less by-products and less phthalic anhydride.

Others have attempted to recover liquid phthalic anhydride from the reaction gases of the catalytic oxidation of o-xylene and/or naphthalene without the formation of a solid phase by absorption, wherein the reaction gases are contacted with an organic absorbent (i.e., a mass separating agent) such that the gas is absorbed in the absorbent.

Absorption is described in *Perry's Chemical Engineerings' Handbook Sixth Edition*, McGraw-Hill Book Company, pp. 13–9 and 18–3. Perry describes absorption as "the transfer of a soluble component in a gas-phase mixture into a liquid absorbent whose volatility is low under process conditions".

Absorption processes operate on the theory that by introducing either fresh or recycled mass separating agents or absorbents at the top of the absorption zone the absorbents will contact the upflowing reaction gases, wherein the absorbents are then loaded with the desired product and then removed from the absorbent zone as a liquid bottoms.

Therefore, the bottoms product from a phthalic anhydride absorption process would typically include a substantially large concentration of absorbent, phthalic anhydride, maleic anhydride and other by-products of the catalytic oxidation of o-xylene and/or naphthalene. Thereafter, the bottoms stream itself containing substantial amounts of the desired phthalic anhydride is primarily recycled as additional absorbent and a portion is withdrawn for further processing to recover the maleic anhydride from the crude phthalic anhydride for further recycle.

One conventional absorption method involves the washing out or dissolving of phthalic anhydride and maleic anhydride from a reaction gas stream by contacting the gas stream with either a dibutyl phthalate or dipropyl phthalate absorbent. This method is disadvantageous since the absorbent or mass separating agent must be successively subjected to distillation, crystallization, and purification before it can be returned for further absorption. Moreover, the absorbent contaminates the resulting phthalic anhydride requiring additional downstream separation.

Still others have used tetradecane, petadecane and hydrocarbons primarily consisting of $C_{26}$ to $C_{44}$ paraffins as mass separating agents (i.e. absorbents). These too introduce outside impurities into the crude phthalic anhydride product.

U.S. Pat. No. 4,285,871 (Keunecke et al.), which issued on Aug. 25, 1981, discloses a process for the continuous separation of phthalic anhydride from the reaction gas of the catalytic oxidation of o-xylene and/or naphthalene wherein the reaction gas is treated with a maleic anhydride-based absorbent (i.e., mass separating agent) containing from 0 to 85% by weight phthalic anhydride. Due to the larger pumparound rates required to remove heat from the gas, the material balance of the overall system according to Keunecke '871 suggests that the concentration of phthalic anhydride which exits the absorber vessel is essentially the same as that contained in the maleic anhydride-based absorbent. As such, the phthalic anhydride concentration discharged from the bottom of the absorber vessel is between about 0 to 85 wt. %, based on the total amount of phthalic anhydride contained in the reaction gas. Additionally, a large portion of this liquid phthalic anhydride is continuously being recycled back to the absorption vessel with the large recycle absorbent stream. Recycling of liquid phthalic anhydride back to the absorbent vessel decreases the effectiveness of the method disclosed in the present invention, i.e., separation of phthalic anhydride from the reaction gas.

U.S. Pat. No. 4,285,870 (Keunecke et al.), which issued on Aug. 25, 1981, discloses a process for the continuous separation of phthalic anhydride from the reaction gas of the catalytic oxidation of o-xylene and/or naphthalene which comprises treating the reaction gas in a first absorption stage with an absorbent (i.e., mass separating agent) comprising benzoic acid and phthalic anhydride, and in at least one additional absorption stage with a liquid, maleic anhydride-based absorbent containing from 0 to about 90% by weight phthalic anhydride. The phthalic anhydride concentration discharged from the bottom of the absorber vessel as a liquid according to Keunecke '870 is between about 0 to 90 wt. % (preferably 40–75 wt. %), based on the rates provided in the example. Keunecke '870 also teaches away from the separation process of the present invention since it, like Keunecke '871, recycles liquid phthalic anhydride together with substantial quantities of both a benzoic acid and/or maleic anhydride absorbent.

Because of the recycling of liquid phthalic anhydride with the absorbent, neither Keunecke '870 nor Keunecke '871 are able to attain a high weight percent of phthalic anhydride concentration in the bottoms stream taken from the absorbent vessel as does the rectification method according to the present invention. This is due to the fact that the absorbent process requires the recycling of substantial amounts of a mixture of liquid maleic and phthalic anhydride (i.e., the absorbent) which acts to absorb the upflowing phthalic anhydride and maleic anhydride gases and take them out as bottoms liquids together with the recycled absorbent.

A fundamental disadvantage of the above described absorption processes is they require rather expensive absorbent recovery and recycle systems in order to maintain the maleic anhydride material balance, within acceptable process conditions such that the amount of these by-products leaving the overall phthalic anhydride recovery system is not greater than the amount of these by-products contained in the reaction gas of the catalytic oxidation of o-xylene and/or naphthalene.

In order to maintain the material balance of the by-products of the catalytic oxidation of o-xylene and/or naphthalene, both U.S. Pat. Nos. 4,285,870 and 4,285,871 incorporate expensive and sophisticated maleic anhydride recovery systems. According to both these patents, the gas leaving the absorption zone contains so much maleic anhydride that is necessary to recover the maleic anhydride by scrubbing the gas stream with water or an aqueous maleic acid solution in a scrubbing column at a temperature in the range between 30° C. to 50° C. The water or maleic acid absorbent is fed to the scrubber and enriched there to about 40% by weight. It then passes from the scrubbing column into a thin-layer evaporator, in which the solution is concentrated to about 100% by weight maleic acid. The maleic acid passes from the thin-layer evaporator into a dehydrator wherein the acid is dehydrated into maleic anhydride. A portion of the maleic anhydride is taken overhead from the dehydrator and returned to the second stage of the absorption column to maintain the maleic anhydride material balance. In Keunecke '871, 0.4 kg maleic anhydride per kilogram of recovered phthalic anhydride is scrubbed, dehydrated and returned to the second stage absorption column. The process according to the present invention does not require the extremely complex and expensive maleic anhydride or by-product recovery scheme for capturing and recycling maleic anhydride, as disclosed in Keunecke '870 and '871, when taken overhead as a vapor stream from the rectification tower.

The present inventors have discovered that it is more economical and much more efficient to treat the vapor phase oxidation reaction gases by rectification, whereby a liquid oxidation reaction product having a phthalic anhydride concentration of between about 50 to 100 wt. %, more preferably 90 to 100 wt. %, is recovered as bottoms and the maleic anhydride and other light by-products are taken out as vapor overhead. Moreover, the separation methods of the present invention maintain the maleic anhydride material balance and do not require the use of an expensive absorbent recovery system as required in the absorbent systems of Keunecke '870 and '871, and also avoids the need to recycle a substantial portion of the phthalic anhydride bottoms stream back into the absorbent zone for the purpose of assisting in the absorption of upflowing gases (except for temperature and concentration control purposes). Recycling of liquid phthalic anhydride is obviously counter-productive in any process which is attempting to purify the phthalic anhydride from its original reaction gases. Also, the rectification tower process permits separation at the higher end of the 50–100 wt. % phthalic anhydride range which significantly reduces the amount of downstream fractionation required to produce a substantially pure phthalic anhydride product of about 99.7 wt. %.

As such, the continuous liquid recovery process of the present invention does not utilize an absorption process to separate a liquid phthalic anhydride product from the reaction gases of the catalytic oxidation of o-xylene and/or naphthalene. Instead, the present inventors have discovered that by contacting a vapor phase oxidation product gas with a by-product(s) stream of the recovery process which has a freezing point which is lower than the freezing point of pure phthalic anhydride in a rectification tower, a crude liquid phase product containing 50 to 100 wt. % phthalic anhydride can be readily separated from a vapor stream having maleic anhydride and other light by-products contained in the gas.

The substantial technical differences between using absorption versus rectification for separating out phthalic anhydride from a vapor phase oxidation gas product without the formation of an intermediate solid phase can be understood by comparing the vapor to liquid weight ratios (V/L) in the absorbent tower against the V/L for the rectification tower. For example, the V/L for the absorbent tower of Keunecke '871, as calculated from the example provided therein is 0.3 to 0.7. The rectification tower of the present invention exhibits a V/L ratio of between 5 to 20, more preferably 8 to 15. That is, due to the substantial pumparound or recycling of the bottoms stream which is required in any absorbent case, its V/L ratio is only a fraction of that which occurs during rectification. The low V/L ratio in the absorbent case of Keunecke '871 clearly demonstrates that due to these high pumparound rates the absorbent tower is not providing any noticeable degree of separation of liquid phthalic anhydride from a vapor phase maleic anhydride, such as that recited in the present invention.

Therefore, the present inventors have developed a unique process wherein crude liquid phthalic anhydride having a phthalic anhydride concentration in the range of between 50 to 100 wt. % can be taken as bottoms from a rectification tower, thereby permitting operation at the higher end of the phthalic anhydride concentration range which requires substantially less maleic anhydride recovery from the crude liquid phthalic anhydride then that which is required using an absorbent step as the initial step in treating the vapor phase oxidation product.

The present invention also allows for maintaining the maleic anhydride material balance of the overall recovery system by controlling the liquid phase compositions and their freezing points by refluxing or recycling a condensed portion of the overhead from the rectifier. The material balancing afforded by the rectifying process according to the present invention avoids the need to provide a costly downstream absorbent recovery system comprising a scrubber, evaporator, dehydrator and distiller for the purpose of recovering sufficient maleic anhydride to maintain a material balance wherein the amount of maleic anhydride leaving the system is not greater than the amount which enters the process in the initial reaction gas.

The present invention accomplishes this material balance by partially condensing and refluxing a condensed liquid by-products stream of primarily maleic anhydride, benzoic acid and citraconic anhydride at a temperature sufficient to avoid solidification of the condensate and/or the condensing of a separate water phase. Moreover, the vapor phase oxidation product is cooled directly in the present invention. In Keunecke '870 and '871, the heat is removed indirectly by cooling the recycle absorbent streams. This indirect cooling method has the disadvantage of requiring large liquid pumparound rates.

SUMMARY OF THE INVENTION

A process for recovering phthalic anhydride as a liquid from a vapor phase oxidation product which comprises mixing the vapor phase oxidation product having a temperature of about 130° C. (266° F.) or greater with a mixed stream comprising maleic anhydride and/or at least one compound selected from the group consisting of: phthalic anhydride, citraconic anhydride and benzoic acid in a contacting means, i.e., a rectification tower, such that a substantial portion of the phthalic anhydride contained within the vapor phase oxidation product transfers from the vapor phase to a liquid phase and the by-products contained in the mixed stream which are more volatile than phthalic anhydride transfer from the liquid phase to the vapor phase and so that a vapor-to-liquid weight ratio in the range between about 5 to 20 is maintained, thereby forming a liquid phase phthalic anhydride product having a phthalic anhydride concentration in the range between about 50–100 wt. %, more preferably 90–100 wt. %, and a vapor phase by-products stream.

The mixed stream is preferably a by-product stream which results from the separation of vapor phase by-products from the liquid phase phthalic anhydride product. Moreover, the by-product stream must have a freezing point which is lower than the freezing point of pure phthalic anhydride in order to effectively separate liquid phthalic anhydride from a vapor phase oxidation product. The mixed stream typically comprises about 0 to 25 mole % phthalic anhydride, about 0 to 50 mole % benzoic acid, about 0 to 20 mole % citraconic anhydride, and about 40 to 100 mole % maleic anhydride.

A preferred embodiment according to the present invention involves a process for recovering phthalic anhydride as a liquid from a vapor phase oxidation product which comprises: (a) cooling the vapor phase oxidation product to a temperature of about 130° C. or greater; and (b) delivering the vapor phase oxidation product to a contacting or rectification means which is capable of causing the vapor phase oxidation product to come into contact with at least one by-product stream having a freezing point which is lower than the freezing point of pure phthalic anhydride such that a substantial portion of the phthalic anhydride contained within the vapor phase oxidation product transfers from the vapor phase to a liquid phase and the by-products contained in the by-products stream which are more volatile than phthalic anhydride transfer from the liquid phase to the vapor phase and so that a vapor-to-liquid weight ratio in the range between about 5 to 20 is maintained, thereby forming a liquid phase phthalic anhydride product having a phthalic anhydride concentration in the range between about 50–100 wt. % phthalic anhydride, and a first vapor stream comprising off-gases, maleic anhydride and other by-products. The rectification means also separates the liquid phase phthalic anhydride product from the first vapor stream. This process may, optionally, include an external means for cooling the first vapor stream to a temperature in the range between about 25° C. to 80° C. (77°–176° F.), thereby forming a first by-product stream and a second vapor stream; separating the first by-product stream from the second vapor stream; and recycling at least a portion of the first by-product stream as reflux to an upper section of the rectification means; whereby an absorbent recovery system to maintain the material balance of the phthalic anhydride recovery process is eliminated.

Optionally, the liquid phase phthalic anhydride product is taken as bottoms and separated into a crude phthalic anhydride stream and a second by-product stream. Thereafter, the second by-product stream is typically cooled to a temperature in the range between about 40° C. to 120° C. (104°–248° F.) and at least a portion may be recycled back to the rectification means.

The rectification means is preferably a low pressure drop gas/liquid contactor which comprises at least 2 equilibrium stages, preferably 3 to 10 equilibrium stages.

Optionally, at least a small portion (i.e., 0–10%) of the liquid phase phthalic anhydride product of step (b) is recycled to the rectification means for composition and freezing point control.

The rectification means according to this embodiment may, optionally, include an internal cooling and separating step disposed at the upper section thereof, wherein the first vapor stream is cooled to a temperature in the range between about 25° C. to 80° C. (77°–176° F.) at or near the upper section of the contacting means, thereby forming a first by-product stream and a second vapor stream; separating the first by-product stream from the second vapor stream; and condensing or returning at least a portion of the first by-product stream to the intermediate and/or lower sections of the rectification means.

The process for separating phthalic anhydride from a vapor phase oxidation product may also include a by-product (e.g., maleic anhydride) recovery step which includes the following steps: mixing the second vapor stream with an absorbent to form an absorbent containing by-product stream; separating the absorbent containing by-product stream into a desorbed by-product stream and a concentrated absorbent stream; and mixing the desorbed by-product stream with a by-product stream. Alternatively, a maleic anhydride recovery process such as water scrubbing can also be used. One such water scrubbing process is described in Keunecke '870 and '871, which are incorporated herein by reference.

This process for separating an anhydride product in a rectification tower having a vapor-to-liquid weight ratio in the rectification tower between about 5 to 20 and a phthalic anhydride bottoms concentration in the range between about 50 to 100 wt. % from a vapor phase oxidation product by mixing and cooling the vapor phase oxidation product with recycled by-products which have freezing points lower than the freezing point of pure anhydride is also applicable for recovery of crude products other than phthalic anhydride such as maleic anhydride, trimellitic anhydride, benzoic acid and pyromellitic dianhydride.

DESCRIPTION OF THE PREFERRED EMBODIMENTS

A continuous process for recovering phthalic anhydride (PAN) in a liquid phase from a vapor phase oxidation product of o-xylene, naphthalene or the like, and compressed air is hereafter described.

The freezing point of pure phthalic anhydride is 131° C. (268° F.). Conventional switch condensers operate by cooling the vapor phase oxidation product below this temperature to plate out solid phase phthalic anhydride on the heat exchange tubes within each switch condenser.

According to the present invention, the formation of crude liquid phthalic anhydride product without the presence of an intermediate solid phase phthalic anhydride is accomplished by contacting the vapor phase oxidation product with recycled by-products which have lower freezing points than pure phthalic anhydride, whereby the operating temperatures are always above the freezing point of the liquid phase. It is preferable that the contacting occur in a rectification tower so that a vapor-to-liquid weight ratio within the contacting tower is maintained in the range between about 5 to 20, more preferably 8 to 15.

Figure 1:
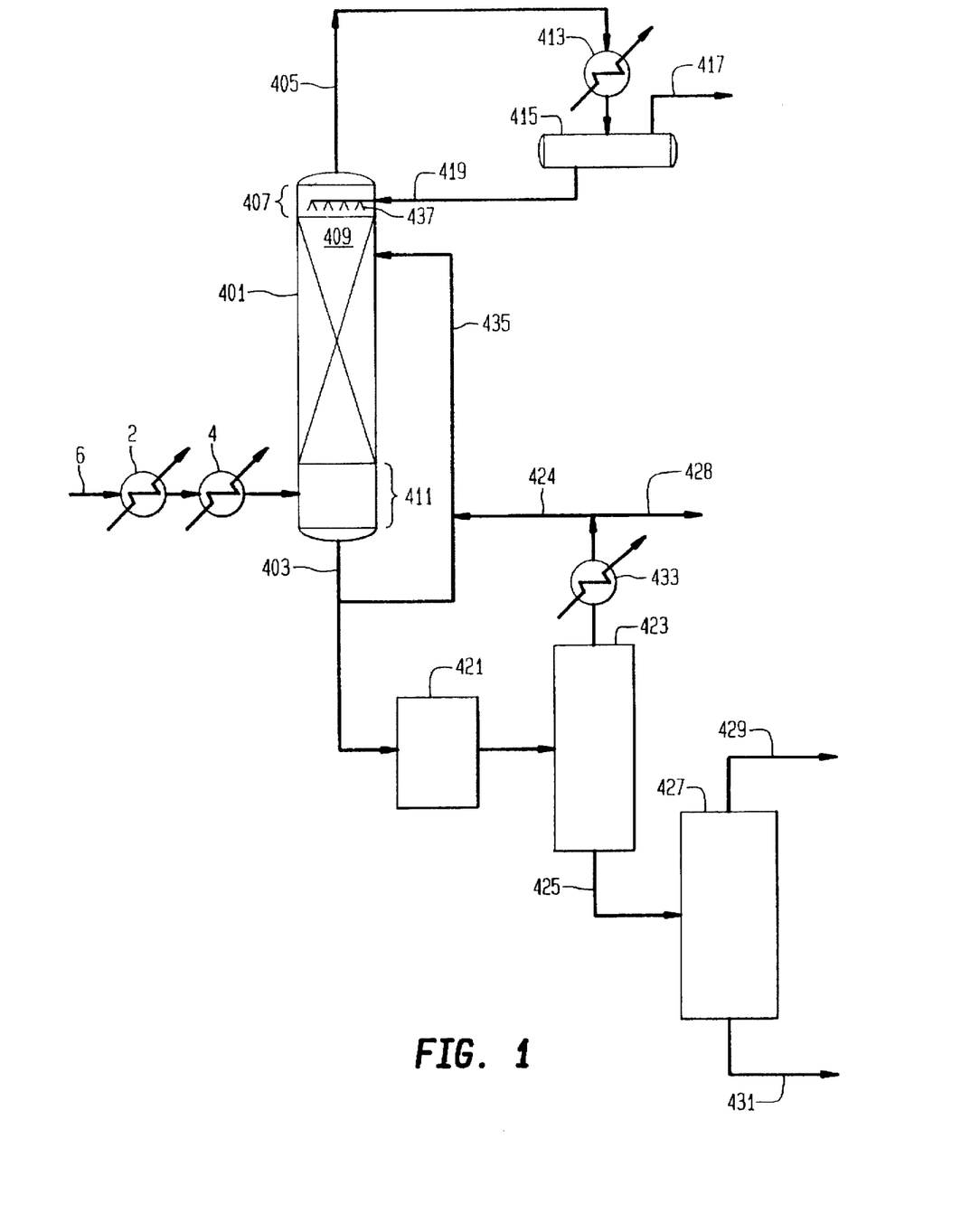
FIG. 1 is a schematic diagram of the phthalic anhydride recovery process in accordance with the preferred embodiment of the present invention wherein a low pressure gas/liquid contactor rectification tower is used in conjunction with external cooling and separating devices for recycling refluxed by-products back to the rectification tower.
Figure 2:
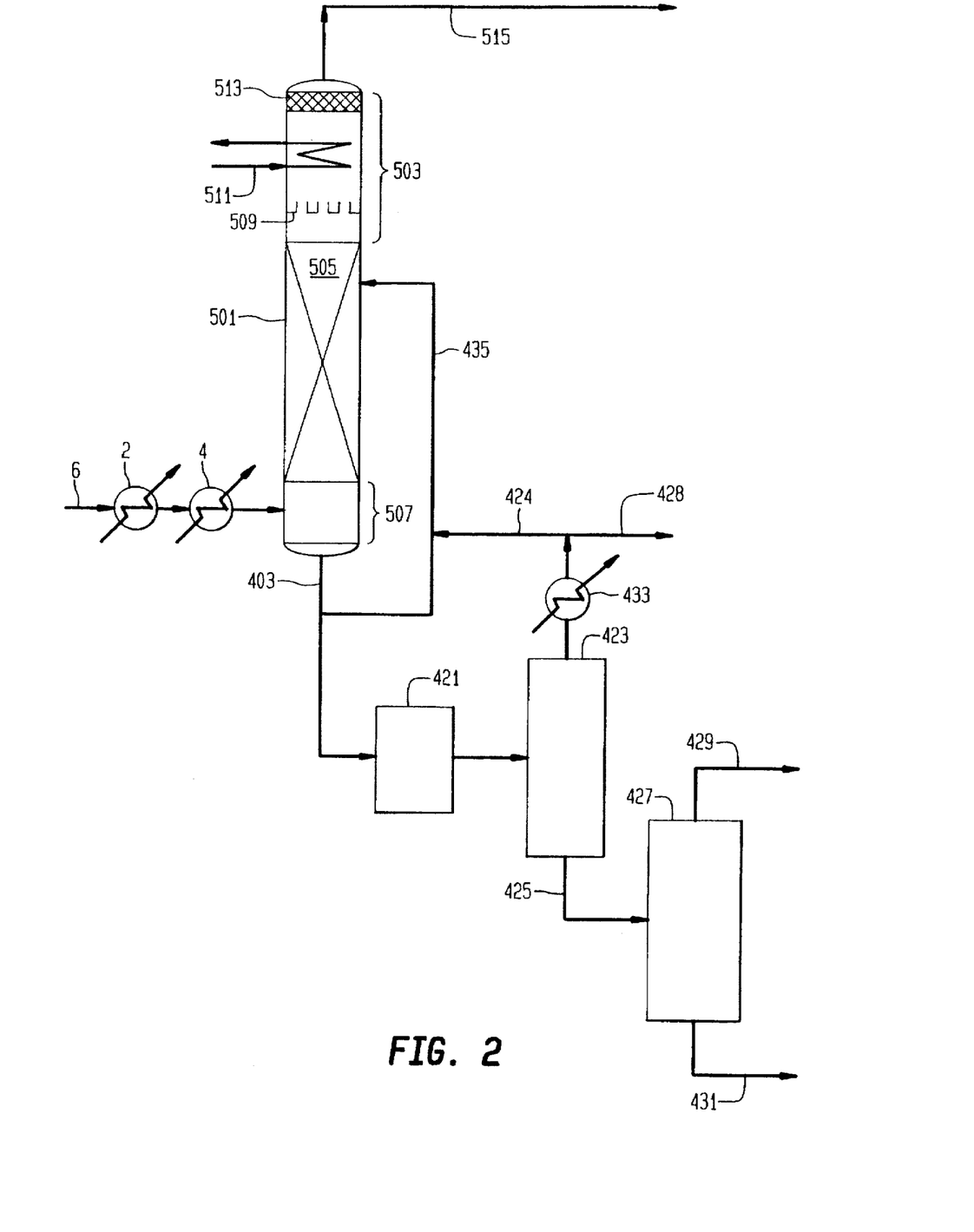
FIG. 2 is a schematic diagram of the phthalic anhydride recovery process in accordance with another embodiment of the present invention wherein an integrated contactor/condenser rectification tower includes an internal reflux section for recycling refluxed by-products back to the rectification section.
Figure 3:
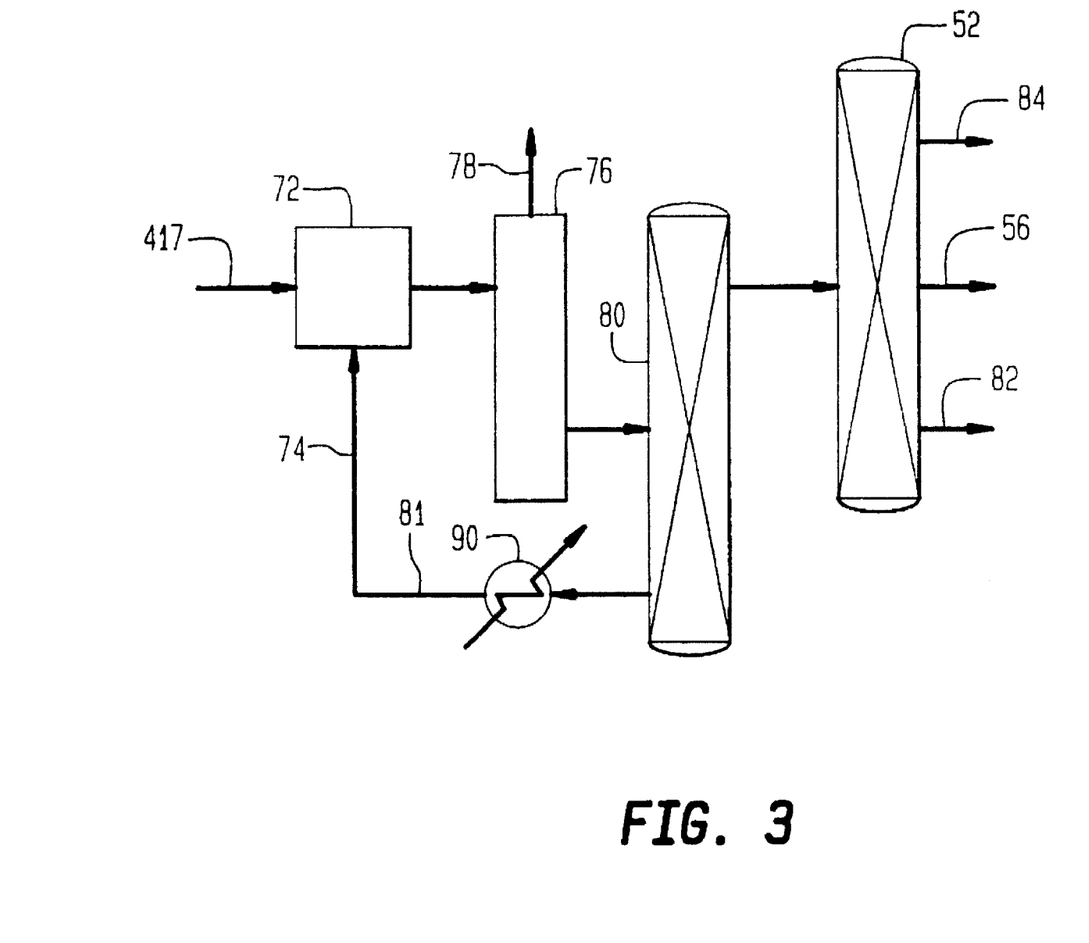
FIG. 3 is a schematic representation of a maleic anhydride recovery system which can be attached to receive the cooled and separated vapor overhead from the processing scheme shown in either FIG. 1 or 2.

The preferred embodiment according to the present invention involves the configurations depicted in FIGS. 1 and 2. These figures pertain to the use of a contacting or packed tower having either an internal or external cooling/condensing system. FIG. 3 depicts the unique process that can be used to recover maleic anhydride from the vapor phase overheads taken from the processes described in FIGS. 1 and 2.

FIG. 1 describes a process for recovering phthalic anhydride as a liquid from a vapor phase oxidation product. The vapor phase oxidation product of o-xylene, naphthalene, and/or any other material capable of being catalytically converted to phthalic anhydride is passed via conduit 6 through heat exchangers 2 and 4 wherein the vapor phase oxidation product is cooled to a temperature of about 130° C. (266° F.) or greater, preferable in the range between about 130° C. to 177° C. Temperatures higher than 130° C. are less desirable because the additional heat is rejected to cooling water and greater rectifier condenser surface area is required. The cooled vapor phase oxidation product is delivered from conduit 6, following cooling to a temperature no lower than about 130° C., to rectifier or contacting means 401 which is capable of causing the vapor phase oxidation product to come into contact with at least one by-product stream having a freezing point which is lower than the freezing point of pure phthalic anhydride and so that a vapor-to-liquid weight ratio in the range between about 5 to 20 is maintained, thereby forming a liquid phase phthalic anhydride product having a phthalic anhydride concentration of between about 50–100 wt. %, preferably between about 85–100 wt. %, more preferably about 90–100 wt. %, and most preferably between about 95–99.8 wt. %, and a first vapor stream. Rectifier tower 401 separates the liquid phase phthalic anhydride product from the first vapor stream by means of multiple equilibrium stages, i.e., packing or trays, (not shown) disposed therein. Rectifier tower 401 is typically a low pressure drop counter-current gas/liquid contactor having at least 2 low pressure drop equilibrium stages, preferably 3 to 10.

It should be kept in mind that despite operating below the freezing point of phthalic anhydride there is no formation of a solid phase anywhere within rectifier tower 401 due to the choice of operating conditions.

The liquid phase phthalic anhydride product is removed from rectifier tower 401 as bottoms via conduit 403, while the first vapor stream is removed from rectifier tower 401 as overhead via conduit 405. Rectifier tower 401 has an upper section 407, an intermediate section 409 and a lower section 411.

The first vapor stream which is taken as overhead from rectifier tower 401 has a temperature in the range between about 115° to 135° C. (239°–275° F.) at a pressure in the range between about 0.10 to 0.14 MPa (14.7–20 psia).

The first vapor stream taken overhead via conduit 405 is passed through a heat exchanger or low pressure drop gas cooler 413 where it is cooled to a temperature in the range between about 25° C. to 80° C. (77°–176° F.), thereby forming a first by-product stream and a second vapor stream. This mixed phase stream is then delivered to a vapor/liquid disengaging drum 415 (with or without a de-entrainment screen) wherein the first by-product stream is separated from the second vapor stream. The second vapor stream is then taken out overhead via conduit 417 for either maleic recovery (for sales) according to FIG. 3 or disposal via incineration. At least a portion of the first by-product stream is taken out as bottoms from drum 415 via conduit 419 and recycled as reflux to upper section 407 of rectifier tower 401. This first by-product stream preferably contains about 55 to 90 mole % maleic anhydride, about 0 to 20 mole % citraconic anhydride, about 0 to 25 mole % phthalic anhydride, and about 0 to 35 mole % benzoic acid.

The liquid phase phthalic anhydride product which is removed from the rectifier tower as bottoms preferably has a concentration of between about 50–100 wt. %, more preferably between about 90–100 wt. %, and most preferably between about 95–99.8 wt.%, phthalic anhydride.

The liquid phase phthalic anhydride product passes via conduit 403, optionally, into at least one decomposer 421 which operates under a slight vacuum (about 700 mm Hg absolute) and high temperatures (e.g., 260° C. (500° F.) to convert the small amount of phthalic acid that is present to phthalic anhydride. Thereafter, the liquid phase phthalic anhydride product is pumped from decomposer 421 to a light ends column or fractionation column 423 wherein a second by-product stream comprising low-boiling by-products, e.g., maleic anhydride, citraconic anhydride and benzoic acid, along with a small amount of phthalic anhydride are removed at the top of fractionation column 423, cooled via heat exchanger 433, and at least a part of this stream is optionally returned to rectifier tower 401 as a second by-product stream via conduits 424 and 435 with the remainder of the stream being purged via conduit 428 from the system to remove benzoic acid. Crude phthalic anhydride is taken as bottoms from fractionation column 423 and is optionally fed via conduit 425 to a second fractionation column 427 wherein substantially pure phthalic anhydride is removed from the top of fractionation column 427 via conduit 429, while heavy products are removed from the bottom via conduit 431.

Optionally, a small portion (i.e., 0–10%) of the liquid phase phthalic anhydride product removed as bottoms from rectifier tower 401 via conduit 403 is recycled via conduit 435 to rectifier tower 401 for temperature and concentration control in the tower.

FIG. 2 depicts an integrated rectifier tower/cooler condenser unit 501 which may be used in place of rectifier tower 401, cooler 413 and separator 415 of FIG. 1. Integrated unit 501 comprises a upper section 503, an intermediate section 505 and lower section 507.

Liquid phase oxidation product is carried via conduit 6 through heat exchangers 2 and 4 where it is cooled to a temperature no lower than about 130° C. before being sent to lower section 507 of integrated rectifier unit 501. Intermediate section 505 of integrated rectifier unit 501 comprises a low pressure drop gas/liquid contactor having at least 2, preferably 3 to 10 equilibrium stages. Upflowing cooled vapor phase oxidation product contacts a downflowing recycled by-product stream from upper section 503 as it passes through intermediate section 505 causing liquid phase phthalic anhydride to return to lower section 507 while a first vapor phase stream passes through liquid redistributor 509 into upper section 503. While in upper section 503, the first vapor stream is cooled via cooling coils 511 to a temperature in the range between about 25° C. to 80° C., thereby forming a first by-product stream and a second vapor stream. The first by-product stream is returned or recycled to the liquid redistributor and thereafter flows downwardly into intermediate section 505 so as to come into contact with upflowing vapor phase oxidation product, as discussed above. The second vapor stream passes through a vapor/liquid disengaging section disposed at the top of upper section 503. The disengaging section may optionally include a de-entrainment screen 513 wherein any residual liquid phase first by-product stream is separated from the second vapor stream before the second vapor stream is taken overhead via conduit 515 for either maleic recovery (for sales) as shown in FIG. 3 and/or incineration.

The liquid phase containing phthalic anhydride passes through integrated rectifier unit 501 in a downward direction until it reaches lower section 507 where it is removed from integrated rectifier unit 501 as bottoms via conduit 403. The liquid phase phthalic anhydride product is then finished in decomposer 421, fractionation tower 423 and fractionation tower 427 as described above.

Overall recovery of the phthalic anhydride from the reactor effluent gas (i.e., vapor phase oxidation product) is approximately 99.7% for both processes described in FIGS. 1 and 2.

Optionally, maleic anhydride in the second vapor phase stream may be recovered in accordance with the unique maleic anhydride recovery process depicted in FIG. 3, wherein the second vapor phase stream is passed via conduit 417 to mixing vessel 72 where it is contacted with dihexylphthalate, or any other ester having a similar boiling point. The ester absorbs approximately 70% of the maleic anhydride which is present in the vapor phase. The maleic anhydride/ester mixture from vessel 72 is then passed to a flash unit 76. The residual vapor is separated and sent via conduit 78 to an incinerator (not shown). The liquid from flash unit 76 containing the absorbed maleic anhydride is separated from the ester via distillation in fractionation column or tower 80. This minimizes the amount of ester in the overhead maleic anhydride stream and especially in recycle stream 56. Virtually all of the ester remaining in the recovered maleic anhydride is removed via purge stream 82. Ester in recycle stream 56 would be purged as a heavy along with the phthalic anhydride residue, unchanged, but would increase the quantity of residue for disposal. The desorbed ester is cooled in heat exchanger 90, and recycled to mixing vessel 72 via conduit 74.

The maleic anhydride recovered from the absorption step in fractionation column 80 is sent to fractionation column 52 optionally along with overhead stream 428 from fractionation column 423. Fractionation column 52 has three product streams, i.e., bottoms, overhead and a recycle side stream. The bottoms are taken out via conduit 82 and primarily include benzoic acid and any heavier components not rejected from fractionation column 50. Unlike other recovery systems, essentially all of the benzoic acid in the reactor effluent gas may be recovered and concentrated in purge stream 82. By adjusting the amount of benzoic acid purged, the benzoic acid content in recycle stream 56 and 424 can be controlled to optimum levels. Although not identified, trace components in this bottoms stream have been shown to cause color problems if not removed from the final purge stream. Essentially all of the ester that goes overhead in column 80 is rejected to this purge stream. The side stream 56 is an impure maleic anhydride recycle stream (i.e., a by-product stream) which contains no significant amounts of phthalic anhydride. Overhead 84 is a higher purity maleic anhydride stream suitable for upgrading for commercial sale.

The sidestream of column 52 is preferably recycled via line 56 to the top section of column 401 and/or maleic anhydride can, optionally, be recovered for sales and/or further purification.

The maleic anhydride recovery process described above is unique since only a portion of the maleic anhydride is recovered requiring only one contacting stage compared to multiple stages in other absorption processes. This process also takes advantage of the fact that the phthalic anhydride and other heavies (i.e., trimellitic anhydride and phthalide) are extremely low and thus do not build-up in the absorber circuit, thereby minimizing absorbent purge and make-up.

Instead of esters, an alcohol such as hexyl alcohol or isopropyl alcohol could be used as make-up to the maleic anhydride recovery section. An alcohol which is capable of forming the monoester in-situ from maleic or phthalic anhydride and eventually forming the diester with similar adsorption properties to dihexyl phthalate would be a satisfactory substitute for the esters in the absorption of maleic anhydride.

Figure 4:
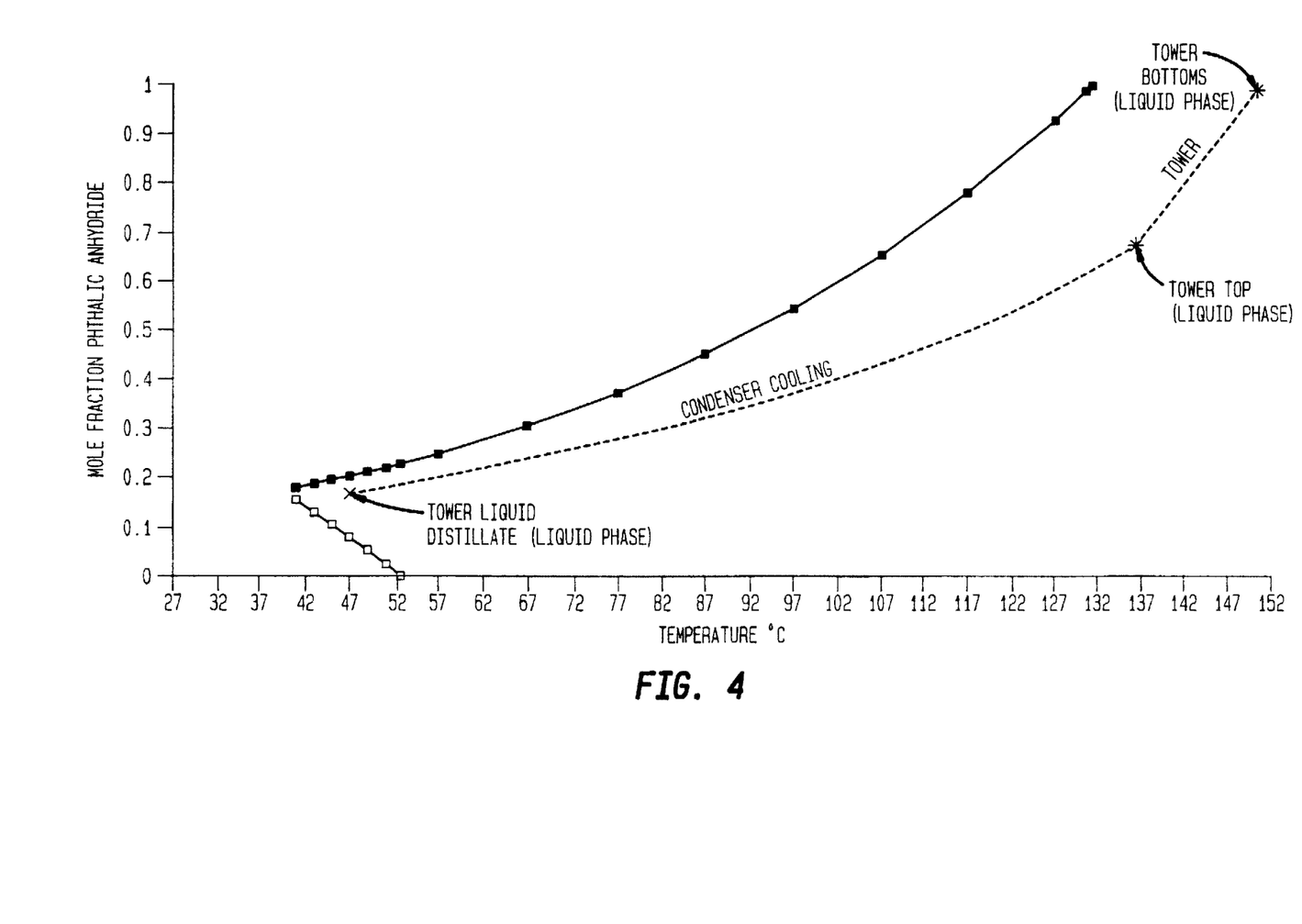
FIG. 4 is a graph comparing the freezing point of phthalic anhydride/maleic anhydride binary mixtures with that of typical operating conditions for the phthalic anhydride recovery processes shown in FIG. 1 and 2.

FIG. 4 is a graph comparing the freezing points of phthalic anhydride/maleic anhydride binary mixtures, with that of typical operating conditions for the processes shown in FIGS. 1 and 2. This FIG. 4 illustrates how the tower and condenser compositions can be controlled to ensure that the freezing point of the liquids are always below the operating temperatures.

This unique process may also be extended to recover other anhydrides and acids such as maleic anhydride, trimellitic anhydride, pyromellitic anhydride, benzoic acid etc. from vapor phase oxidation products without the formation of a solid phase intermediate.

What is claimed is:

1. A process for recovering phthalic anhydride as a liquid from a vapor phase oxidation product which comprises mixing said vapor phase oxidation product having a temperature of about 130° C. or greater with a first stream comprising maleic anhydride and at least one compound selected from the group consisting of: citraconic anhydride, benzoic acid and phthalic anhydride in a contacting means such that a substantial portion of the phthalic anhydride contained within said vapor phase oxidation product transfers from the vapor phase to a liquid phase and a substantial portion of the by-products contained in said first stream which are more volatile than phthalic anhydride transfer from the liquid phase to the vapor phase and wherein a vapor-to-liquid weight ratio in the range between about 5 to 20 is exhibited within said contacting means, thereby forming a liquid phase phthalic anhydride product having a phthalic anhydride concentration in the range between about 50–100 wt. %.

2. The process according to claim 1 wherein said phthalic anhydride concentration is in the range between about 90–100 wt. %.

3. The process according to claim 2 wherein said phthalic anhydride concentration is in the range between about 95 to 99.8 wt. %.

4. A process for recovering phthalic anhydride as a liquid from a vapor phase oxidation product which comprises:

(a) cooling said vapor phase oxidation product to a temperature of about 130° C. or greater; and (b) delivering said vapor phase oxidation product to a contacting means which is capable of causing said vapor phase oxidation product to come into contact with at least one by-product stream having a freezing point which is lower than the freezing point of pure phthalic anhydride such that a substantial portion of the phthalic anhydride contained within said vapor phase oxidation product transfers from the vapor phase to a liquid phase and a substantial portion of the by-products contained in the by-product stream which are more volatile than phthalic anhydride transfer from the liquid phase to the vapor phase and wherein a vapor-to-liquid weight ratio in the range between about 5 to 20 is exhibited within said contacting means, thereby forming a liquid phase phthalic anhydride product having a phthalic anhydride concentration in the range between about 50 to 100 wt. %, and a first vapor stream; said contacting means is also capable of separating said liquid phase phthalic anhydride product from said first vapor stream.

5. The process according to claim 4 wherein said phthalic anhydride concentration is in the range between about 90–100 wt. %.

6. The process according to claim 5 wherein said phthalic anhydride concentration is in the range between about 95 to 99.8 wt. %.

7. The process according to claim 4 wherein said contacting means is a low pressure drop counter-current gas/liquid contactor.

8. The process according to claim 7 wherein said low pressure drop counter-current gas/liquid contactor comprises between about 2 to 10 equilibrium stages.

9. The process according to claim 4 further comprising the steps of:

(c) removing said liquid phase phthalic anhydride product from said contacting means as bottoms;

(d) removing said first vapor stream from said contacting means as overhead;

(e) cooling said first vapor stream to a temperature in the range between about 25° C. to 80° C., thereby forming a first by-product stream and a second vapor stream;

(f) separating said first by-product stream from said second vapor stream; and (g) recycling at least a portion of said first by-product stream to the upper section of said contacting means.

10. The process according to claim 9 wherein said first by-product stream comprises about 55 to 90 mole % maleic anhydride, about 0 to 20 mole % citraconic anhydride, about 0 to 25 mole % phthalic anhydride, and about 0 to 35 mole % benzoic acid.

11. The process according to claim 9 wherein said first vapor stream which is taken as overhead from said contacting means has a temperature in the range between about 115° to 135° C. at a pressure in the range between about 0.10 to 0.14 MPa.

12. The process according to claim 9 further comprising the step of separating said liquid phase phthalic anhydride product into a crude phthalic anhydride stream and a second by-product stream.

13. The process according to claim 12 further comprising the steps of cooling said second by-product stream to a temperature in the range between about 40° C. to 120° C.; and recycling at least a portion of said second by-product stream to said contacting means.

14. The process according to claim 9 further comprising the step of recycling between about 0 to 10 wt. % of said liquid phase phthalic anhydride product of step (c) to said contacting means, whereby said liquid phase phthalic anhydride product is only used for temperature and composition control.

15. The process according to claim 4 further comprising the following steps:

(c) cooling said first vapor stream to a temperature in the range between about 25° C. to 80° C. in the upper section of said contacting means, thereby forming a first by-product stream and a second vapor stream;

(d) separating said first by-product stream from said second vapor stream in said upper section; and (e) transferring the first by-product stream to the top of said contacting means;

(f) removing said liquid phase phthalic anhydride product from said contacting means as bottoms; and (g) removing said second vapor stream from said contacting means as overhead.

16. The process according to claim 4 wherein said vapor phase oxidation product in step (a) is cooled to a temperature in the range between about 130° C. to 177° C.

17. The process according to claim 9 further comprises mixing said second vapor phase stream with an absorbent, thereby forming a maleic anhydride/absorbent stream; and desorbing said maleic anhydride/absorbent stream to form an enriched maleic anhydride stream and a concentrated absorbent stream, recycling at least a portion of said enriched maleic anhydride stream to steps (e), (f) or (g).

* * * * *